United States Patent [19]

Kensey et al.

[11] Patent Number: 5,192,302
[45] Date of Patent: Mar. 9, 1993

[54] PLUG DEVICES FOR SEALING PUNCTURES AND METHODS OF USE

[75] Inventors: Kenneth Kensey, Chester Springs; John Nash, Downingtown, both of Pa.

[73] Assignee: Kensey Nash Corporation, Exton, Pa.

[21] Appl. No.: 783,645

[22] Filed: Oct. 28, 1991

Related U.S. Application Data

[63] Continuation-in-part of Ser. No. 445,315, Dec. 4, 1989, Pat. No. 5,061,274.

[51] Int. Cl.⁵ .............................................. A61B 17/04
[52] U.S. Cl. ................................... 606/213; 606/215; 604/15
[58] Field of Search ........ 606/213, 215, 216, 228–232; 604/13, 15, 49, 51, 60, 158; 623/1, 11, 12; 600/32

[56] References Cited

U.S. PATENT DOCUMENTS

| | | | |
|---|---|---|---|
| 2,711,173 | 6/1955 | Seidler | 604/15 |
| 2,879,770 | 3/1959 | Graham, Jr. | 604/15 |
| 2,934,068 | 4/1960 | Graham, Jr. et al. | 604/15 |
| 3,762,413 | 10/1973 | Hawke | 604/15 |
| 3,874,388 | 4/1975 | King et al. | 623/11 |
| 4,390,018 | 6/1983 | Zukowski | 604/51 |
| 4,744,364 | 5/1988 | Kensey . | |
| 4,852,568 | 8/1989 | Kensey . | |
| 4,890,612 | 1/1990 | Kensey . | |
| 5,021,059 | 6/1991 | Kensey et al. | 606/232 |
| 5,041,129 | 8/1991 | Hayhurst et al. | 606/232 |
| 5,053,046 | 10/1991 | Janese | 606/215 |
| 5,061,274 | 10/1991 | Kensey | 606/213 |

*Primary Examiner*—Stephen C. Pellegrino
*Assistant Examiner*—Ralph A. Lewis
*Attorney, Agent, or Firm*—Caesar, Rivise, Bernstein, Cohen and Pokotilow, Ltd.

[57] ABSTRACT

Closure devices and methods of use for sealing a small, e.g., percutaneous, incisions or punctures. The closure device may take many forms an basically comprises a somewhat elongated plug having a deformable distal end portion including a free end to which a thin retraction filament is connected. The closure device is arranged to be introduced into the body of the being through the incision or puncture by an introducer so that the distal portion of the plug is located on one side of said tissue and its proximal portion is located on the other side of that tissue, with the filament extending through the incision or puncture. The filament is arranged to be grasped and pulled in the proximal direction to deform the distal portion of the plug so that it cannot pass back through the incision or puncture, whereupon the puncture or incision is sealed by the deformed distal portion of the plug. The distal portion of the plug is non-hemostatic so that when the closure is used to seal an incision or puncture in a blood vessel it will not produce any blood clots within the vessel.

32 Claims, 6 Drawing Sheets

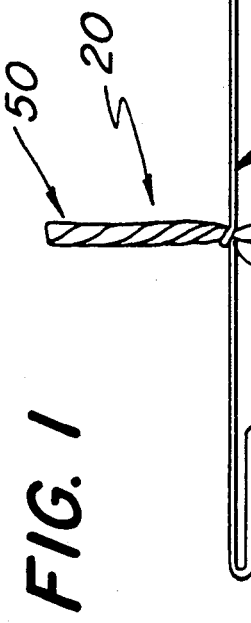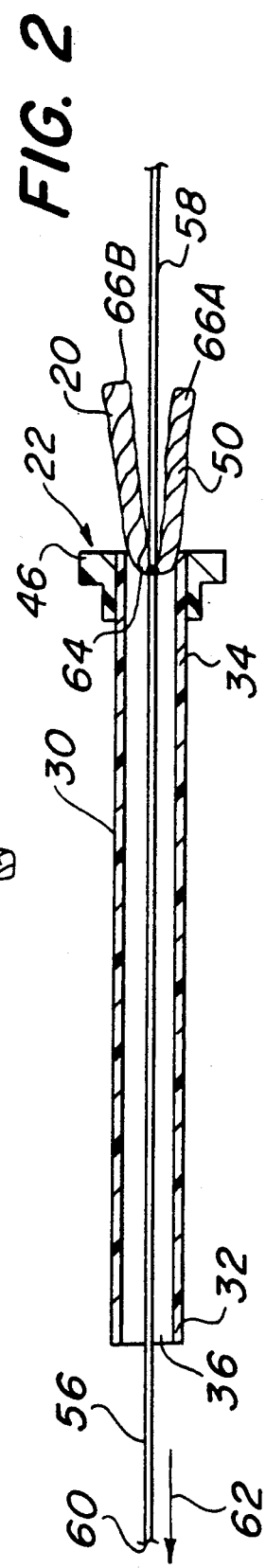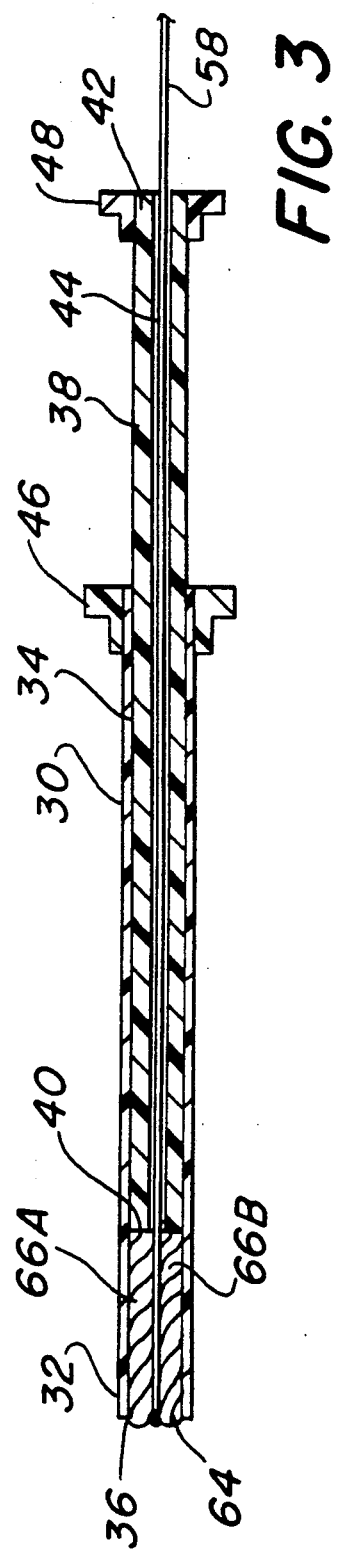

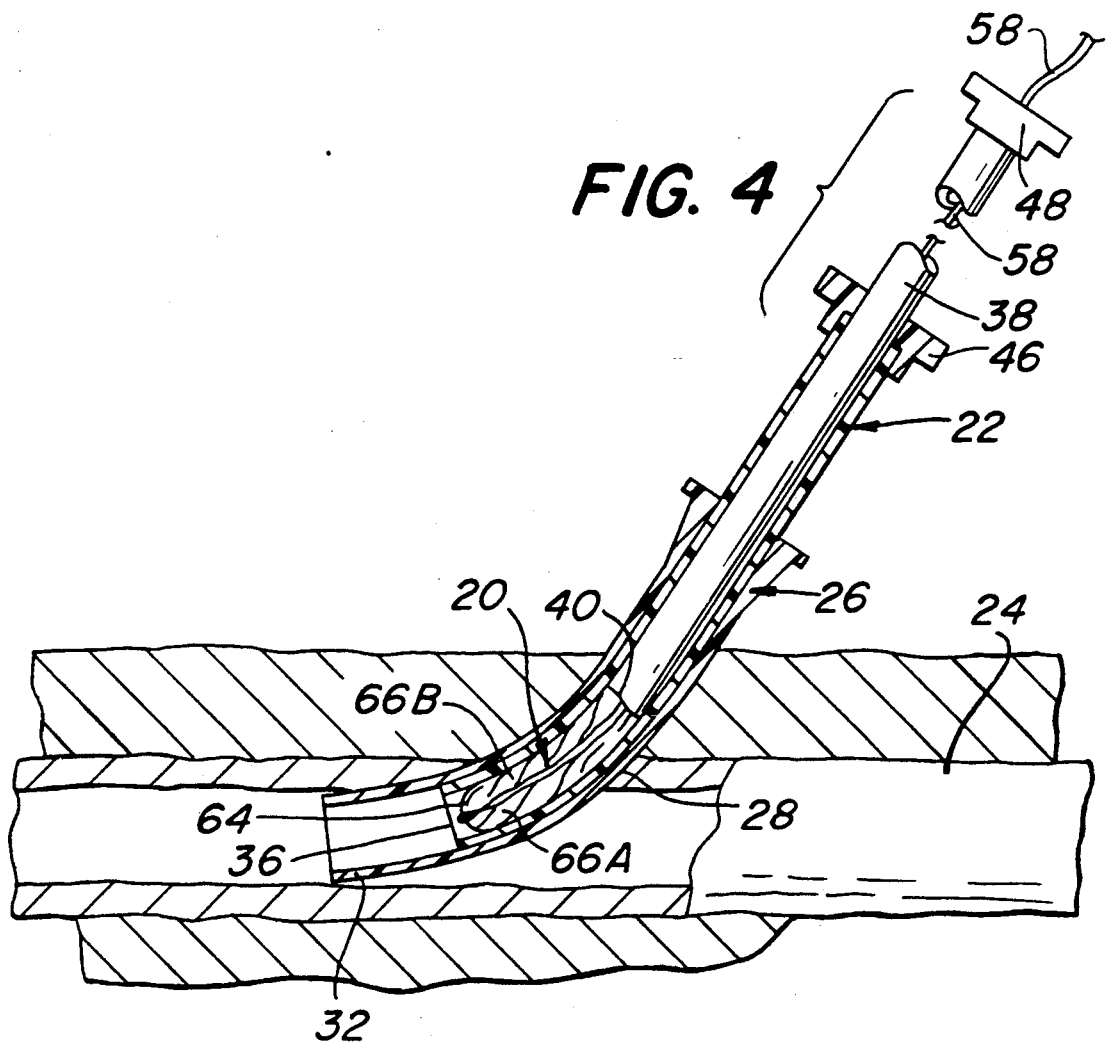
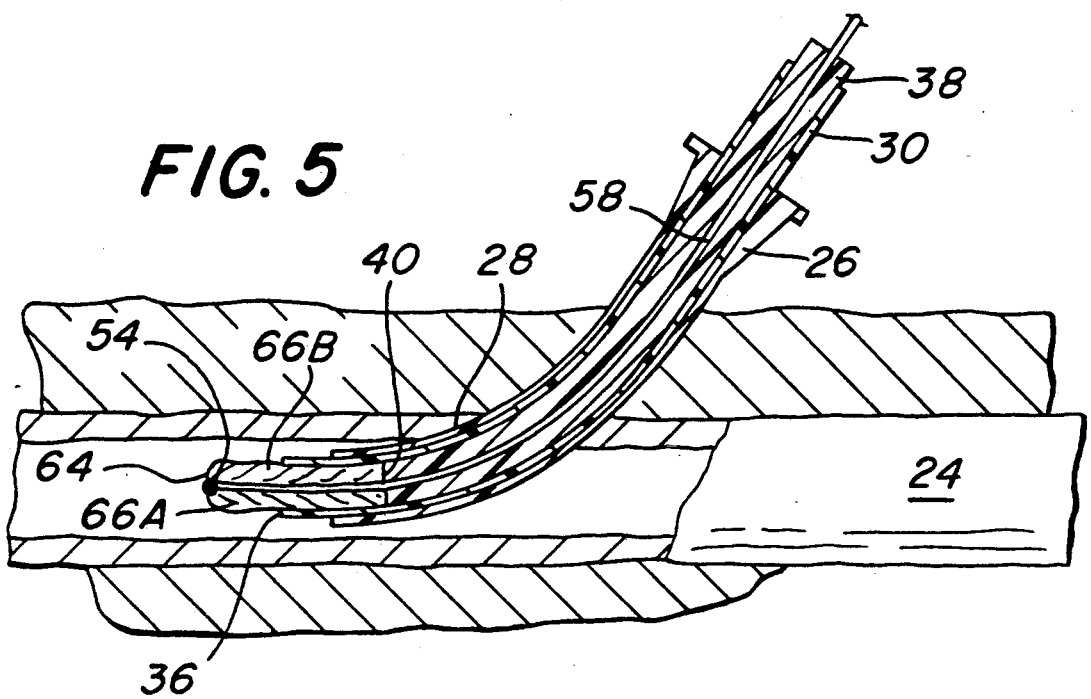

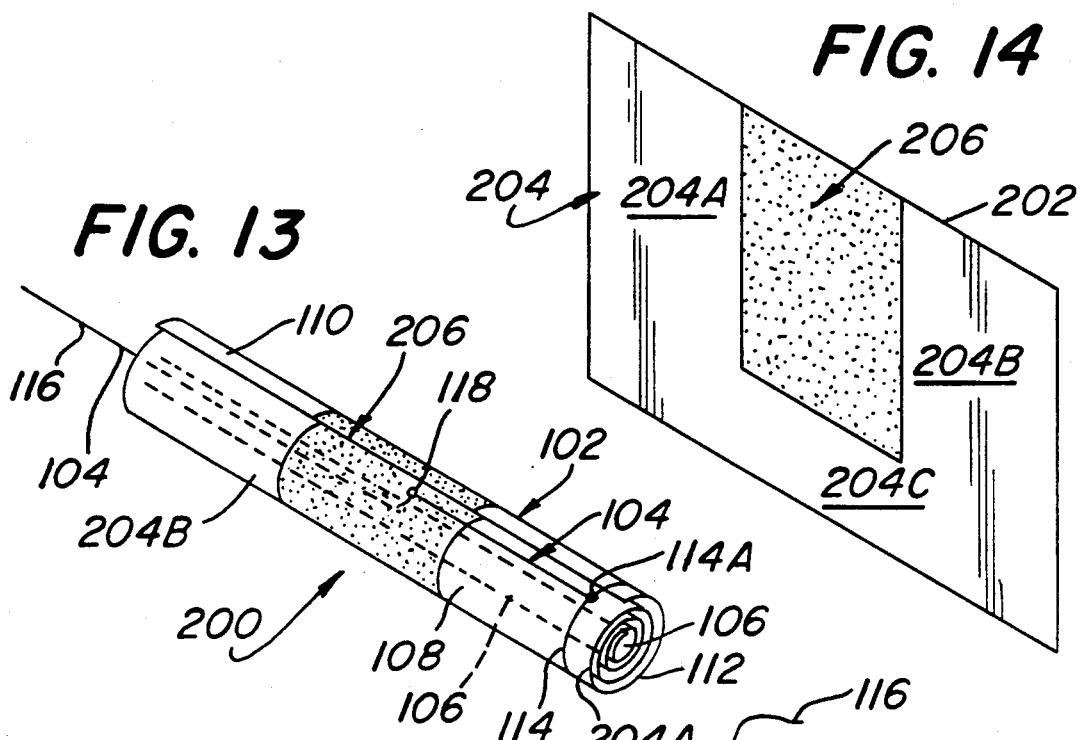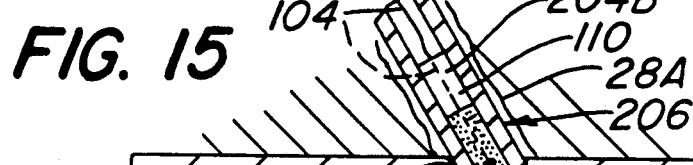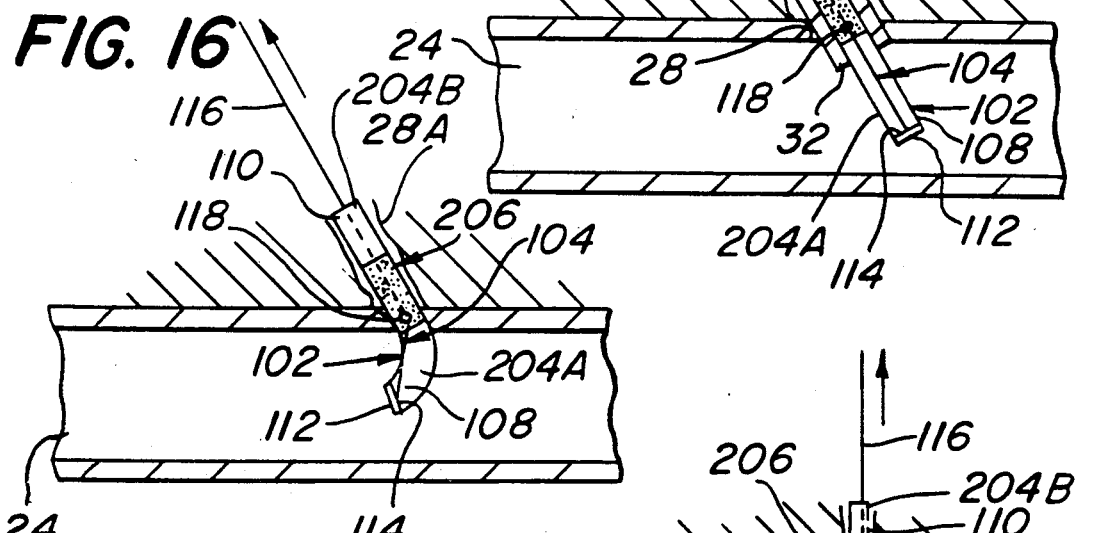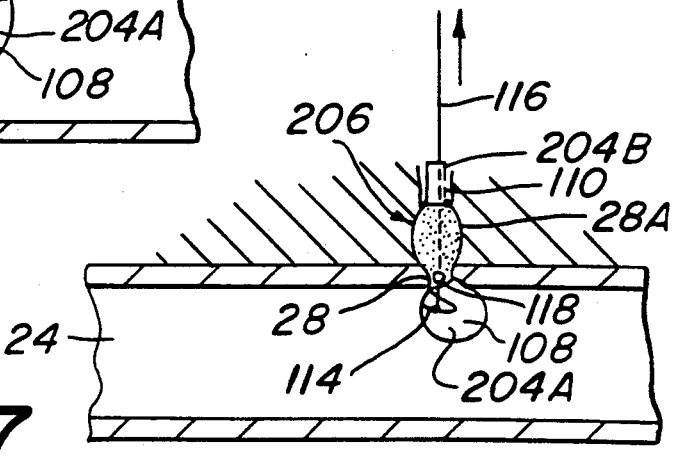

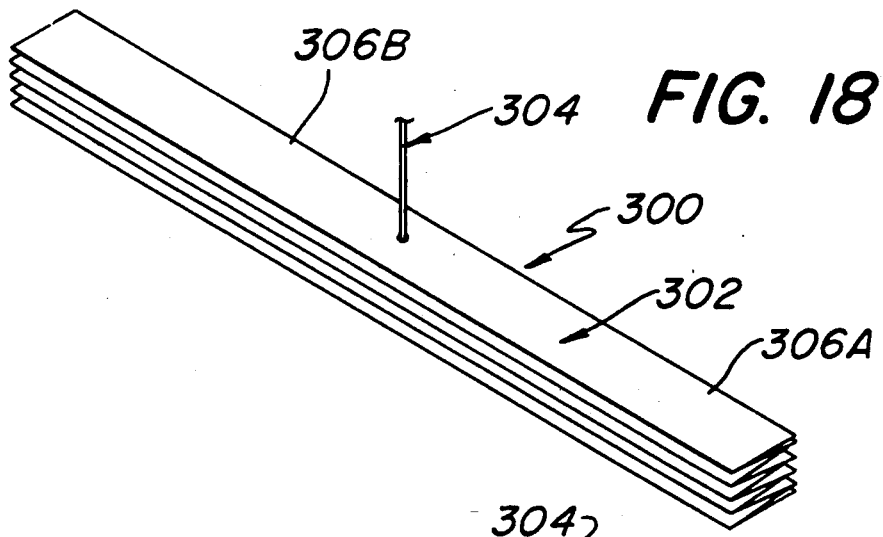
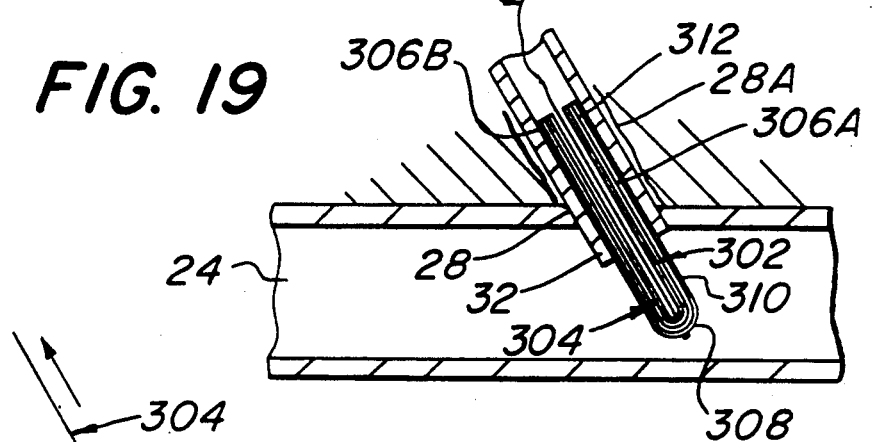
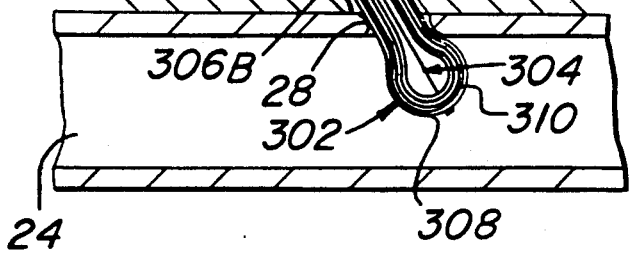
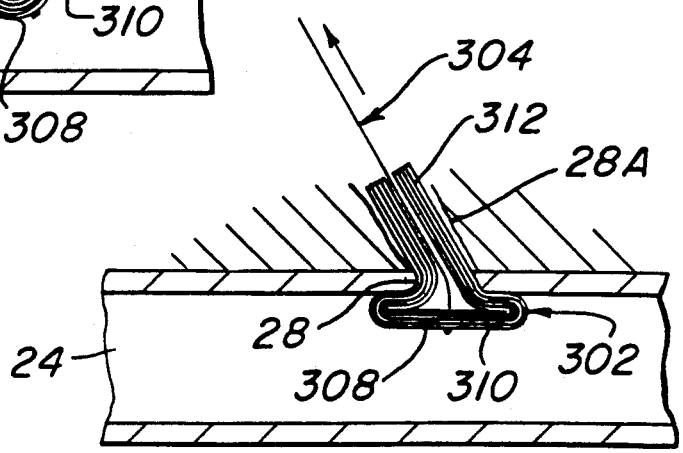

PLUG DEVICES FOR SEALING PUNCTURES AND METHODS OF USE

This application is a Continuation-in-Part of U.S. patent application Ser. No. 07/445,315, filed on Dec. 4, 1989, now U.S. Pat. No. 5,061,274, for Plug Device for Sealing Opening and Method of Use, which is assigned to the same assignee as this invention and whose disclosure is incorporated by reference herein.

This invention relates generally to medical devices and methods of use, and more specifically to devices and methods of use for sealing percutaneous openings or incisions in the body of a living being.

BACKGROUND OF THE INVENTION

In U.S. Pat. Nos. 4,744,364 and 4,852,568, assigned to the same assignee as this invention, there is disclosed a device for sealing an incision or puncture in tissue separating one portion of the body of a living being from another portion, e.g., a puncture in a blood vessel, duct or lumen, of a living being. Also disclosed are methods of use of that device. The device basically comprises an elongated tubular body having an outlet at its distal end. The distal end of the device is arranged to be inserted, such as percutaneously, through the puncture. In the case where the puncture is an artery or other blood vessel, the outlet is inserted through the puncture so that it is located within the blood vessel's interior. An expandable closure is disposed within the device's tubular body and is formed so that it is held in a compact or compressed configuration within the tubular body. The tubular body also includes an ejector in the form of a plunger-like member arranged to force the closure out of the outlet into the portion of the being's body contiguous with the opening, e.g., within the interior of the blood vessel, whereupon the closure automatically expands to form an enlarged tissue engagement surface.

A retraction filament is secured to the closure to enable it to be pulled fully into the puncture after the device's tubular body has been withdrawn so that the engagement surface of the closure intimately engages the inner surface of the tissue contiguous with the puncture.

In accordance with one aspect of the disclosure of those patents, the filament is held taut or otherwise secured and placed on the patient's skin to hold the closure in position in the puncture. Preferably, the closure and filament are each formed of some biodegradable material to enable them to be left in place. When the closure is used for sealing punctures or incisions in blood vessels it is constructed so that when it is open (i.e., in its expanded state) and in place sealing the puncture it doesn't appreciably block the flow of blood through the blood vessel.

In U.S. Pat. No. 4,890,612, assigned to the same assignee as this invention, there is disclosed a device for sealing a puncture or incision formed percutaneously in tissue separating two internal portions of the body of a living being and a method of use of that device. The device basically comprises a closure or plug formed of a material which when located within the puncture or incision expands automatically to engage the tissue contiguous therewith to seal the puncture and incision from the flow of body fluid therethrough. The closure disclosed in that application basically comprises a holding member, a filament, and a sealing member. The holding member is an elongated body, constructed like a toggle, and preferably formed of a biodegradable, thermoplastic polymer, such as polyglactide. The toggle is molded onto the distal end of the filament. The filament is also biodegradable, and preferably formed of polyglactide suture. The filament, being flexible, enables the toggle to pivot to various orientations with respect to it. The sealing member basically comprises a cylindrical plug, preferably formed of a compressed foam, which is highly absorbent and which when disposed within the body swells in excess of its compressed diameter.

The closure is arranged to be used by an instrument to place it within the puncture or incision to be sealed. The instrument includes a tubular member in which the closure is disposed so that the toggle is oriented with its longitudinal axis parallel to the longitudinal axis of the tubular member. When so disposed the toggle compresses the portion of the distal end of the sealing member. The filament extends backward from the toggle through the sealing member.

The instrument is introduced into the puncture or incision in the artery or any body tissue (e.g., the liver, gall bladder, lung, heart, etc.) until its outlet is at the desired position. In the case of sealing an artery, the outlet of the instrument is positioned so that it is within the artery. The instrument is then operated to expel the closure member from the tubular member. Once the closure is expelled, the instrument is held in this position for a short period of time to allow the foam at the tip of the closure, that is the distal end portion of the closure, to swell. This action effectively tilts the toggle. The instrument may then be withdrawn and the closure's filament retracted. This action pulls the closure's plug portion back through the puncture or incision in the artery wall until its toggle portion engages the inner surface of the artery wall to stop further retraction. As the toggle comes into engagement with the arterial wall, it effects the compression of the distal end portion of the sealing member. Moreover, the proximal end portion of the sealing member extends into the puncture or incision in the subcutaneous tissue to a point closely adjacent the skin. These actions effectively seal the puncture or incision from the passage of blood therethrough.

Other alternative embodiments of a plug or closure are also disclosed in U.S. Pat. No. 4,890,612. Those alternative embodiments basically comprise a preformed foam plug having an enlarged distal end portion serving as the holding member and a proximately located, rod-like portion serving as a sealing member. A retraction filament is secured to the sealing member. The closure is preferably formed of a dense collagen foam, with long collagen fiber reinforcements, so that it has a high expansion ratio (wet-to-dry) and good mechanical wet strength. Those alternative closures are also held within the instrument in a compressed state, with the holding portion located adjacent the instrument's outlet, and are inserted into the incision or puncture in the same manner as described heretofore. Once the closure is ejected out of the instrument, the holding portion of the closure swells upon contact with blood in the artery. The closure, now swollen, hangs up at the puncture or incision within the arterial wall, with the enlarged holding member portion engaging the inner surface of the interior wall and the sealing portion extending fully through the puncture or incision into the subcutaneous tissue. The filament is retracted to fully seat the closure in place so that the sealing portion extends fully through the puncture or incision in the arterial wall and with its proximal end located within the subcutaneous tissue closely adjacent the skin.

While the foregoing closures are generally suitable for their intended purposes, they still leave something to be desired from the standpoint of simplicity of construction and ease of use.

OBJECTS OF THE INVENTION

Accordingly, it is a general object of this invention to provide incision or puncture closure devices and methods of use which overcomes the disadvantages of the prior art.

It is a further object of this invention to provide simply constructed incision or puncture closure devices and methods of use for quickly, easily, and effectively sealing a puncture or incision in tissue separating one portion of the body of a living being from another portion.

It is a still a further object of this invention to provide simply constructed incision or puncture closure devices and methods of use for quickly, easily, safely, and effectively sealing a puncture or incision in an artery in a living being.

SUMMARY OF THE INVENTION

These and other objects of this invention are achieved by providing puncture or incision closure devices and methods of use for sealing a small incision or puncture in tissue, e.g., an artery, separating one portion of the body of a living being from another portion thereof to prevent the flow of bodily fluid, e.g., blood, through the incision or puncture.

The closure devices are each arranged to be introduced through the incision or puncture by an introducer, e.g., an instrument having a tubular portion terminating in a free end through which the plug device may be expelled.

The closure devices basically comprise plug means and retracting means. The plug means basically comprises a generally elongated member having a distally located portion and a proximally located portion. The distally located portion is deformable and includes a free end. The retracting means, e.g., a thin, generally flexible filament, is secured to the distally located portion of the plug means adjacent the free end thereof.

The closure device is arranged to be introduced into the body of the being through the incision or puncture by the introducer so that the distal portion of the plug means is located on one side of said tissue and its proximal portion is located on the other side of that tissue, with the retraction means extending through the incision or puncture.

The retraction means is arranged to be grasped and pulled in the proximal direction to deform the distal portion of the plug means so that the plug means cannot pass back through the incision or puncture and so that the incision or puncture is sealed by the deformed distal portion of the plug means.

In one embodiment of the invention the plug means comprises a tube, e.g., is a rolled up sheet. At least the distal portion of the tube is formed of a non-hemostatic material. The tube has a central passageway. The retraction means comprises a filament which is connected to the distal portion of the tube adjacent the free end thereof and extends along the outside of the distal portion of said tube for a portion of the length of the tube and then passes into the central passageway of the tube and out the proximal portion thereof. This embodiment of the closure device is resistant to the formation of blood clots, and is of particular utility for sealing punctures or incisions in blood vessels, e.g., arteries, since the distal, non-hemostatic portion of the plug will not form any blood clot within the vessel.

In another embodiment of the invention the plug is also in the form of a tube, e.g., a rolled up sheet. In this embodiment the distal portion of the tube is also formed of non-hemostatic material. However at least a portion of the proximal portion of the tube is formed of a hemostatic material. The tube has a central passageway. The retraction means, e.g., filament, is connected to the distal portion of the tube adjacent the free end thereof and extends along the outside of the distal portion of said tube for a portion of the length of the tube and then passes into the central passageway of the tube and out the proximal portion thereof. This embodiment of the plug is particularly suited for sealing incisions or punctures in blood vessels due to the fact that the distal portion is non-hemostatic and thus will not produce blood clots. The hemostatic material at the proximal portion of the tube is arranged to be located within the track of the incision or puncture to serve as a means for anchoring the plug in position once the puncture or incision is sealed by the deformed distal end of the plug means. To best achieve that end the hemostatic material is also preferably expandable, e.g., is crushed collagen.

In yet another embodiment the plug means is in the form of a sheet which is pleated to form an elongated strip The strip is then bent in two to form a bar-like member. The retraction means, e.g., filament, is connected to the apex of the bar-like member, with that apex forming the free end of the distal portion of the plug means. In accordance with this embodiment at least the distal portion of the plug means is formed of a nonhemostatic material. This embodiment of the plug is also resistant to the formation of blood clots, due to the nonhemostatic nature of its distal portion, and is thus also of particular utility for sealing punctures or incisions in blood vessels.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 1 is a side elevational view of the plug device of this invention;

FIG. 2 is a side elevational view, partially in section, showing an initial step of inserting the plug device shown in FIG. 1 into a portion of an instrument in preparation for its use;

FIG. 3 is a side elevational view, partially in section, similar to that of FIG. 1 and showing the final step readying the plug device and the instrument holding it for use to seal an incision or puncture.

FIG. 4 is a side elevational view, partially in section, showing the instrument having the plug device constructed in accordance with this invention therein being inserted into a conventional sheath extending through a percutaneous incision or puncture into an artery to effect the sealing of that incision or puncture;

FIG. 5 is a side elevational view, partially in section, similar to FIG. 4 and showing an intermediate step in the process of sealing the incision or puncture;

FIG. 13 is an isometric view of still another embodiment of the closure or plug of this invention;

FIG. 14 is an isometric view showing the manner by which the closure or plug of FIG. 13 is formed;

FIG. 15 is a side elevational view, partially in section, showing the closure or plug of FIG. 13 being inserted through a percutaneous incision or puncture into an artery to effect the sealing of that incision or puncture;

FIG. 16 is a side elevational view, partially in section, similar to FIG. 15 and showing an intermediate step in the process of sealing the incision or puncture;

FIG. 17 is a side elevational view, partially in section, similar to FIG. 15 and showing the final step in the process of sealing the incision or puncture;

FIG. 18 is an isometric view of still another embodiment of the closure or plug of this invention;

FIG. 19 is a side elevational view, partially in section, showing the closure or plug of FIG. 18 being inserted through a percutaneous incision or puncture into an artery to effect the sealing of that incision or puncture;

FIG. 20 is a side elevational view, partially in section, similar to FIG. 18 and showing an intermediate step in the process of sealing the incision or puncture; and FIG. 21 is a side elevational view, partially in section, similar to FIG. 18 and showing the final step in the process of sealing the incision or puncture.

DETAILED DESCRIPTION OF THE PREFERRED EMBODIMENT

Figure 6:
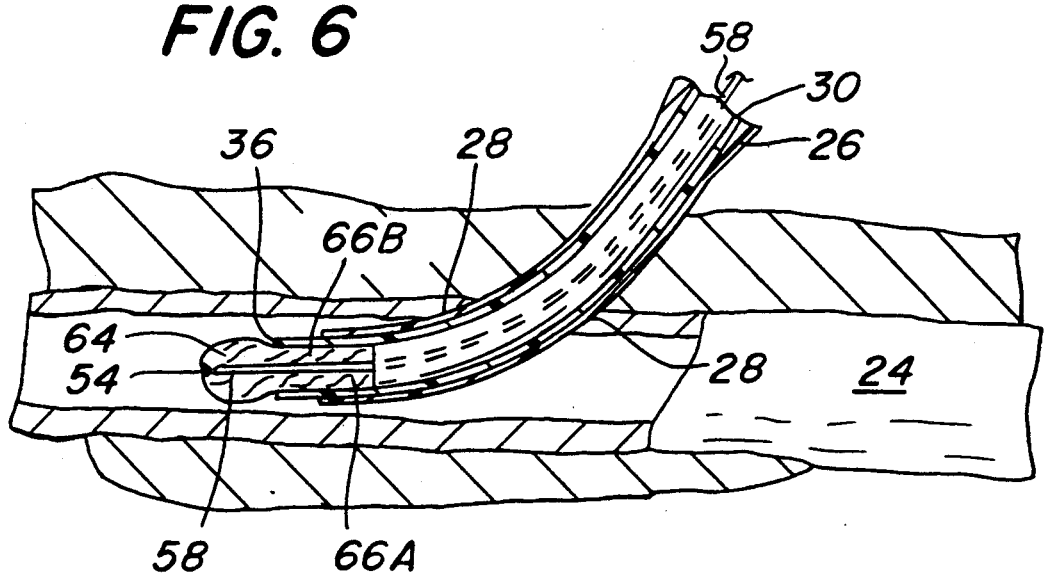
FIG. 6 is a side elevational view, partially in section, similar to FIG. 4 and showing a subsequent intermediate step in the process of sealing the incision or puncture.
Figure 7:
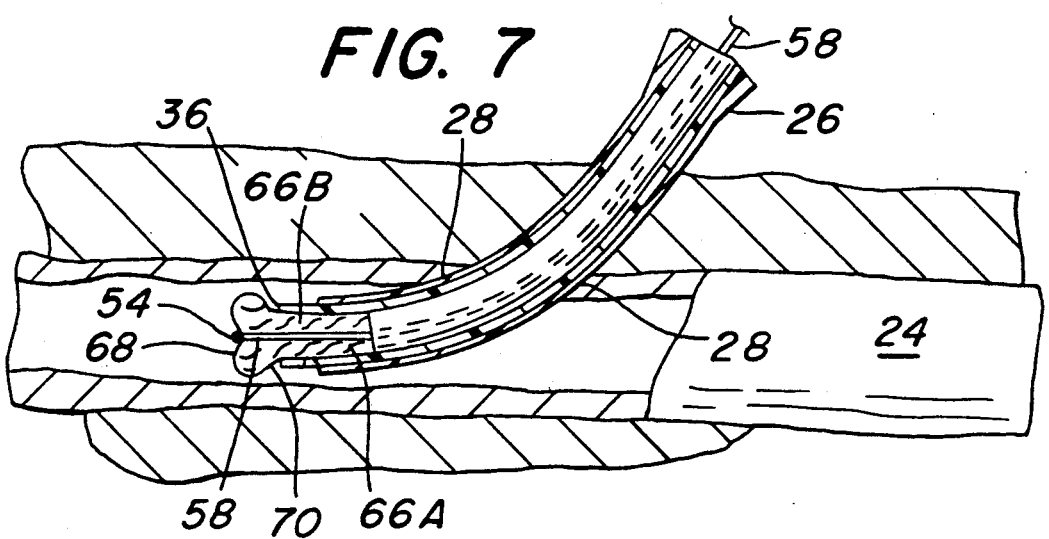
FIG. 7 is a side elevational view, partially in section, similar to FIG. 4 and showing a further subsequent intermediate step in the process of sealing the incision or puncture.

Referring now in greater detail to the various figures of the drawings wherein like reference characters refer to like parts, a closure or plug device embodying the present invention is generally shown at 20 in FIG. 1. The device 20 is arranged to be used to effect the sealing of an incision or puncture or other small opening in any tissue separating two portions of the body of a living being to prevent liquid(s) or body fluid(s) to flow through the incision or puncture. The device 20 has particular utility when used in connection with intravascular procedures, such as angiographic dye injection, balloon angioplasty and other types of recanalizing of atherosclerotic arteries, etc. However, it is to be understood that while the description of the preferred embodiments of the closure (plug) devices contained herein is directed to the closing off of percutaneous incisions or punctures in arteries, such devices have much more wide-spread applications. Thus, the sealing of a percutaneous incision or puncture in an artery shown herein is merely exemplary.

In order to use the device 20 to seal the incision or puncture, the device is arranged to be located within an introducing instrument 22 like that shown in FIG. 3 and which will be described in detail later.

Before describing the device 2 and the instrument 22 for inserting it to seal the incision or puncture, a brief description of a typical, conventional, intravascular surgical procedure, e.g., catheter instrumentation of an artery, utilizing a percutaneous incision or puncture will be given to best appreciate the features of the invention. In such a procedure a cannula of an instrument, such as an angiographic needle (not shown), is inserted percutaneously through the skin into the artery, such as the femoral artery 24 at the situs for the instrument's 22 insertion (See FIG. 4). The needle cannula is held in place and the flexible end of a mini-guidewire (not shown) is then passed through the cannula into the artery to the desired depth (i.e., longitudinal position therealong). Once the mini-guide wire is in place the needle cannula is removed, leaving the guidewire in place. A conventional introducing sheath 26 and an arterial dilator (not shown) are then passed over the guidewire, through the puncture or incision 28 and into the artery 24. The guidewire and then the dilator are removed leaving the sheath in place. The catheter (not shown) or other intravascular instrument (not shown) is then inserted through the introducer sheath 26 and threaded down the artery to the desired intravascular location, e.g., the situs of the atherosclerotic occlusion. Once the intravascular procedure (e.g., angioplasty) has been completed, the catheter is removed. Thereafter, the sheath is removed and the surgeon or other trained person applies digital pressure to the percutaneous puncture until hemostasis has occurred.

The device 20 effects the hemostatic closure of the percutaneous (or any other type of puncture, incision or opening) in the artery or any other tissue separating two portions of the body without necessitating the application of pressure thereto. Thus, once the catheter or intravascular instrument has been removed, but with the introducer sheath 26 left in place, the instrument 22 holding the device 20 of the subject invention is inserted through the sheath, into the artery 24 and operated to expel the device 20 into the artery 24.

As can be seen clearly in FIG. 1, the device 20 basically comprises a closure or plug, whose details will be described later, which is arranged to be drawn into the puncture or incision 28 to seal it. The introducer sheath 26 is then removed and the closure or plug left in place. Due to its construction the closure or plug is ultimately absorbed by the surrounding tissue.

Referring now to FIGS. 2 and 3, the details of instrument 22 will now be described. As can be seen the instrument 22 basically comprises a carrier in the form of a tubular body 30 having a distal end 32 and a proximal end 34. The distal end 32 forms a free end of the instrument and comprises an open outlet 36. The tubular body is preferably constructed of a sufficiently small outside diameter, e.g., 8F (French) and somewhat flexible material, such as polyethylene or polyvinyl chloride, to enable it to be inserted through the introducer sheath 26 into the artery 24, with the tubular body's outlet 36 within the artery 24 distally of the incision of puncture 28 as will be described later. A pusher member 38 is disposed within the tubular member 30. The pusher basically comprises an elongated, cylindrical rod-like member, having a free or distal end 40 and a proximal end 42. A central passageway 44 extends through the pusher. Preferably the pusher is also formed of a relatively flexible material, such as polyethylene or polyvinyl chloride, and is disposed within the interior of the tubular body as shown in FIG. 3 when the instrument is ready for use. The outside diameter of the pusher is slightly less than the inside diameter of the tubular body to enable the pusher to be manually moved, that is slid, down the longitudinal axis of the tubular body, to push or force the closure 20 out of the outlet 36, as will be described later.

The proximal end of the tubular member 30 includes a flange 46 and the proximal end 42 of the pusher 38 includes a similar flange forming a cap 48. The flanges 46 and 48 form portions to be gripped or engaged by the operator's fingers to enable the pusher to be moved (pushed) longitudinally down the tubular member to expel the closure 20, as will be described later.

Referring again to FIG. 1 it can be readily seen that the closure or plug 20 basically comprises a cord 50 and a filament 52. In accordance with one aspect of the preferred embodiment of the invention, the cord comprises a stranded yarn of plural fibers 50A of collagen or some other absorbable material. In particular one exemplary yarn consists of five strands 50A of 0.032 inch (0.81 mm) fibers which are twisted together. The filament 52 is secured to the cord 50 by wrapping it about the midsection 54 of the cord and knotting it thereat. This action forms a pair of filament sections, namely, 56 and 58, with section 56 forming a distally extending section with portion 58 forming a proximately extending portion.

As can be seen clearly in FIG. 2 the plug 20 is arranged to be inserted into the tubular member 30 of the instrument 22 as follows: the distally extending filament portion 56 is inserted through the open proximal end of the tubular member 30 and extended therethrough until its free end 60 extends out of the outlet 36 of the tubular member. The distally extending filament portion 56 is then pulled in the distal direction, like shown by arrow 62, whereupon the cord 50 of the closure 20 enters into the open proximal end of the tubular member. This action causes the cord to fold in half to form a leading or apex portion 64 and a pair of trailing, i.e., proximately extending, wing portions 66A and 66B. The distally extending filament portion 56 is then continued to be pulled in the proximal direction, thereby drawing the folded plug 20 down the tubular member 30 until its apex 64 is immediately adjacent the open end 36 of the tubular member 30. When the plug is in this position (shown in FIG. 3) the proximally extending filament portion 58 extends in the proximal direction from the folded cord 5 through the tube 30 and out its open proximal end. The pusher member 38 is then inserted within the tubular member 30. In particular, the free end of the proximally extending filament portion 58 is introduced into the distally located opening in the central passageway 44 of the pusher and threaded down the central passageway until it extends out of the opening at the flange or head 48 of the pusher. The pusher is then introduced into the proximately located opening in the tubular member and slid down the interior thereof in the distal direction until its 40 free end is located immediately adjacent the wings 66A and 66B of the plug 20. The distally extending filament portion 56 is then cut off or severed from the apex 36 of the cord immediately adjacent the apex. Once this latter action has been achieved the instrument 22 is ready for use.

Operation of the instrument 22 is best understood by reference to FIGS. 4-8 and is as follows: the instrument 22 is inserted within the introducer sleeve 26 so that the free end 32 of the tubular member 30 extends through the puncture or incision 28 like that shown in FIG. 4. The user then engages and pushes on the cap 48 of the pusher with his/her thumb while grasping the flange 46 of the tubular member between his/her fingers. This action slides the pusher in the distal direction within the tubular member 30 so that its free end 40 engages the end of the wing portions 66A and 66B of the plug to force the apex portion 64 of the plug out of the open free end 36 of the tubular member as shown in FIG. 5. The plug is left in this position for a few minutes, whereupon the portion extending into the artery expands slightly in the presence of the liquid, e.g., blood, etc., within the artery, as shown in FIG. 6.

The proximally extending filament portion 58 is then pulled in the proximal direction. This action causes the enlarged portion of the cord's apex to engage the free edge of the opening 36 of the tubular member 30 thereby further radially expanding and flattening that portion to form an enlarged or mushroom shaped head 68.

Figure 8:
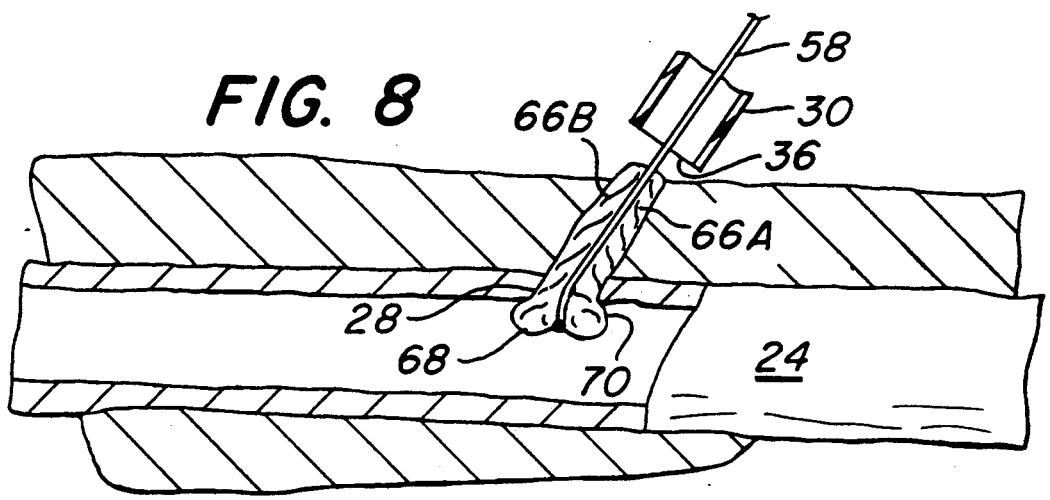
FIG. 8 is a side elevational view, partially in section, similar to FIG. 4 and showing the final step in the process of sealing the incision or puncture.

After the head 68 of the plug 20 has been expanded to its maximum diameter the introducer sleeve 26 is removed from the puncture or incision 28 and the instrument 22 is then withdrawn as shown in FIG. 8. This retraction action (i.e., the removal of the instrument from within the puncture or incision 28) causes the peripheral edge portions 70 on the underside of the enlarged head 68 of the plug to be drawn into close or intimate engagement with the tissue contiguous with the incision or puncture 28 to thereby seal that incision or puncture.

As can be seen in FIG. 8 with the closure in position the head 68 does not take up a substantial portion of the interior of the artery and thus does not block off or otherwise impede the flow of blood therethrough.

When the closure 20 of the subject invention is used to hemostatically seal a puncture or incision in an artery or other vessel, in order to minimize the risk of thrombosis the head of the closure which is exposed to the flow of blood through the artery may be coated with a non-thrombogenic material. Such a material can comprise a waxy coating, such as coconut oil, etc.

As mentioned earlier the cord 50 is formed of a resorbable, e.g., biodegradable, material. In accordance with the preferred embodiment of the invention, the filament 52 is also resorbable, and is preferably a suture of 3-0 size. These features enable the cord and filament to be left in place after hemostasis has occurred, since both will be absorbed by body's tissues thereafter. Accordingly, the plug does not have to be removed after having served its purpose.

Moreover, when the plug of the instant invention is used for sealing punctures or incisions in arteries a conventional clotting agent, such as tissue thromboplastin may be provided in the closure to accelerate hemostasis.

While the plug's cord has been described as comprising a stranded yarn of plural fibers such a construction is merely exemplary of various types of constructions. Thus, the "cord" may merely consist of a strip or bar of some resorbable material which is sufficiently flexible to fold over and form the heretofore described apex and wing portions.

Figure 9:
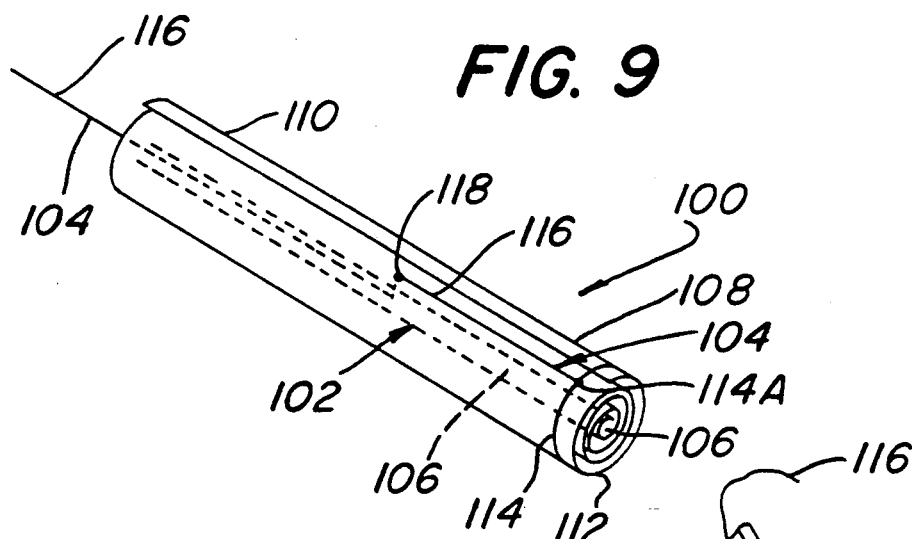
FIG. 9 is an isometric view of another embodiment of the closure or plug of this invention.

Referring now to FIG. 9 an alternative embodiment to the closure device 20 is shown and designated by the reference number 100. As can be seen the closure device 100 basically comprises a plug member 102 and an associated retraction member 104. The retraction member comprises a filament or other strand-like member. The plug member 102 is a generally elongated member having a central passageway 106 extending longitudinally therethrough and has a distally located portion 108 and a proximally located portion 110. The free end of the distally located portion is designated by the reference number 112.

The plug member 102 may be formed in any manner so that it has a longitudinal passageway extending through at least the proximally located portion 110 to receive the filament 104 therethrough as will be described later. In the embodiment of FIG. 9 the plug member 102 is preferably formed of a sheet which is reeled up about a mandrel (not shown) to form a tube. Alternatively the plug may be formed of a rod or bar of material with a longitudinal passageway formed therein and extending through at least the proximally located portion of the rod or bar. Irrespective of the manner by which the plug member is formed, it is preferable that at least its distally located portion is formed of a non-hemostatic material, such as polyglycolic acid, polylactide, polylactic acid, nonthrombogenic collagen, or combinations thereof. Thus, in the embodiment shown in FIG. 9 the tubular member 102 is formed of a sheet of such material which has been rolled up.

The retraction filament 104 is also formed of any suitable, non-hemostatic material, e.g., conventional suture material, an is secured to the distally located portion 108 of the plug member 102 immediately adjacent the free end 112 thereof. In particular, the filament 104 includes a looped portion 114 and an extending portion 116. The looped portion 114 tightly encircles the periphery of the plug member 104 immediately adjacent the free end 112 and is knotted in place by a knot 114A. The extending portion 116 of the filament 104 lies longitudinally along the outer surface of the proximally located portion 110 of the plug member and passes into an opening or hole 118 in an intermediate portion thereof. The opening 118 communicates with the central longitudinal passageway 106. The remainder of the extending portion 116 of the filament 104 then passes through the central passageway 106 and exits at the top end of the plug member 104.

Figure 10:
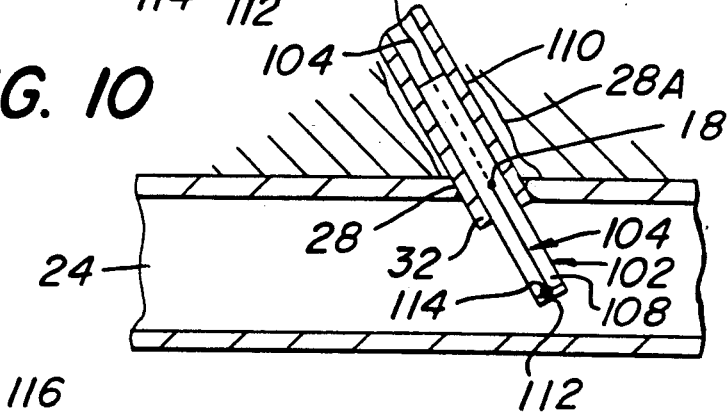
FIG. 10 is a side elevational view, partially in section, showing the closure or plug of FIG. 9 being inserted through a percutaneous incision or puncture into an artery to effect the sealing of that incision or puncture.

The distally located portion 108 of the plug member is deformable, e.g., bendable so that it can be bent back over itself. That action occurs once the closure device 100 is in place within the puncture or incision 28 to be sealed, e.g., the puncture or incision in the artery 24. In particular, the device 100 is introduced by any suitable introducer, e.g., a tubular introducer having an open free end 32 similar to that described heretofore, through the puncture or incision 28 so that the plug's distally located portion 110 is positioned within the interior of the artery and its proximal portion 108 is positioned within the puncture track 28A extending between the outer surface of the artery wall and the patient's skin. In this position the extending portion 116 of the filament 104 passes through incision or puncture track 28 to a point outside the body of the being as shown clearly in FIG. 10. The introducer is then removed from the body of the patient.

Figure 11:
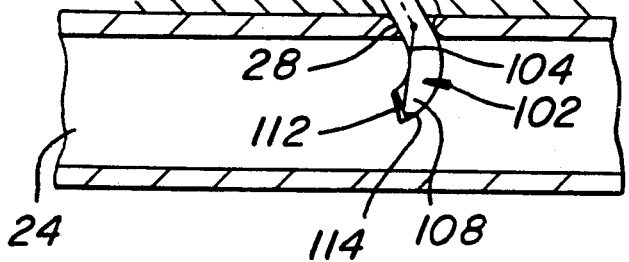
FIG. 11 is a side elevational view, partially in section, similar to FIG. 10 and showing an intermediate step in the process of sealing the incision or puncture.

The externally located extending portion 116 of the filament 104 is then pulled away from the body, i.e., pulled in the proximal direction. Since the filament 104 is connected to the distally located portion of the plug member on the outer surface thereof and extends along that surface until it enters radially into the hole 118 the retraction or pulling on the filament 104 causes the distally located portion of the plug member contiguous with the free end to begin to bend as shown in FIG. 11. The continued pulling on the filament causes the free end 112 of the plug member 102 to bend back over itself and to engage the inner surface of the artery wall contiguous with the incision or puncture 28. This action has the effect of creating a somewhat enlarged head which prevents the plug from exiting the artery through the puncture or incision and which also effectively seals the puncture or incision so that blood cannot flow out of the artery through the puncture or incision.

Figure 12:
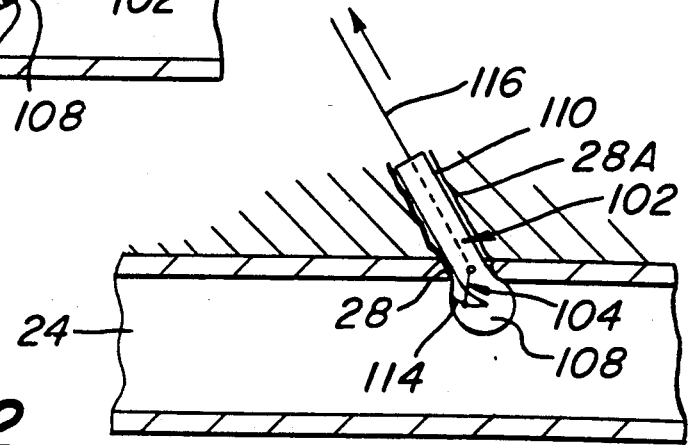
FIG. 12 is a side elevational view, partially in section, similar to FIG. 10 and showing the final step in the process of sealing the incision or puncture.

As can be seen in FIG. 12 with the closure in position its enlarged head does not take up a substantial portion of the interior of the artery and thus does not block off or otherwise impede the flow of blood therethrough. Moreover, by virtue of the fact that the distally located portion of the plug means is non-hemostatic, the portion, e.g., head, of the plug means located within the interior of the artery will not produce any blood clot(s) therein.

In order to hold the closure device 100 in the position as shown in FIG. 12 any suitable holding or locking means can be utilized. Such means may take various forms and be located at various positions. For example, such means may comprise some component located on the skin of the being to hold the filament portion 116, or may comprise a component located within the puncture or incision track 28A to hold the proximally located portion 112 or the filament 116. Moreover, such holding or locking means may comprise a component located within the puncture track 28A to engage the exterior surface of the artery.

In FIG. 13 there is shown yet another alternative embodiment of the closure device of this invention. That closure device is designated by the reference number 200 and is similar in construction and operation to the closure device 100 except that it includes hemostatically operative means to hold or lock closure device 200 in position. In particular the device 200 includes means (to be described hereinafter) to hemostatically hold the proximal portion of the plug means within the incision or puncture track 28A once the incision or puncture in the artery has been sealed.

The construction of the closure 200 is similar to the closure 100. Moreover, the manner by which the sealing of the incision or puncture 28 is accomplished is the same with both of the closure devices 100 and 200. Thus, in the interest of brevity the various components which are common to both of those closure devices will be given the same reference numbers and their construction and operation will not be reiterated in detail hereinafter.

As can be seen in FIG. 13 the closure device 200 basically comprises a somewhat elongated plug member 102 and an associated retraction filament 104. The plug member 102 has a central passageway 106 extending longitudinally therethrough and includes a distally located portion 108 and a proximally located portion 110. The distally located portion 108 terminates in a free end 112.

The tubular plug member 102 of closure device 200 is formed of a sheet of a non-hemostatic material, such as polyglycolic acid, polylactide, polylactic acid, nonthrombogenic collagen, which is reeled up about a mandrel (not shown). However, unlike the sheet forming the plug member 102 of the closure device 100, the sheet forming the plug member 102 of the closure device 200 includes a portion which is hemostatic and a portion which is non-hemostatic. That sheet is shown in FIG. 14 and is designated by the reference number 202. Thus, as can be seen the sheet 202 includes a first section 204 formed of a non-hemostatic material and a second section 206 formed of a hemostatic material. The first section 204 of the sheet 202, when viewed in plan, is generally U-shaped having side portions 204A and 204B and an end portion 204C. The end portion forms what will be referred to later as the "inner" marginal edge of the sheet 202. The second section 206 of the sheet 202, when viewed in plan, is generally rectangular and is located within the confines of the portions 204A, 204B and 204C of the U-shaped section 204.

In accordance with a preferred embodiment of this invention the sheet section 204 is formed of polyglycolic acid, polylactide, polylactic acid, non-thrombogenic collagen, and the sheet section 206 is formed of an expandable material, e.g., crushed collagen.

The sheet 202 is rolled up starting with the inner marginal edge 204C. Thus, when the sheet 202 is completely rolled up the distally located portion 108 of the plug member 102 will be nonhemostatic (it will be formed by a portion 204A of section 204), whereas the intermediate portion of the proximally located portion of the plug member will be hemostatic (it will be formed by a portion of the section 206). The top of the proximally located portion of the plug member will be nonhemostatic (it will be formed by a portion 204B of the section 204). Thus, the hemostatic portion 206 will be held sandwiched between the nonhemostatic portions of the plug member.

Like the closure 100, the distally located portion 108 of closure 200 is deformable, e.g., bendable, so that it can be bent back over itself by pulling on the filament 104, like that described heretofore with reference to closure 100. Moreover, as seen in FIGS. 15-17 the closure device 200 operates in the same manner as previously described, except for the locking or holding of the closure device 200 in place after the incision or puncture 28 in the wall of the artery 24 has been sealed. In this regard, as will be appreciated by those skilled in the art, blood which is in the tissue(s) contiguous with the puncture or incision track 28A will engage the expandable hemostatic material 206 of the plug member located within that track. This action will result in the expansion of the material 206 followed shortly thereafter by hemostasis, thereby locking the proximally located portion 110 of the plug means 200 in place.

In FIG. 18 there is shown yet another embodiment of the closure device of this invention. That device is designated by the reference number 300 and basically comprises plug means 302 and associated retraction means 304. The plug means is formed from a sheet of material which is pleated to form an elongated rectangular strip. The strip is then bent in two to form a pair of legs 306A and 306B which extend parallel and immediately adjacent to each other and which together form a generally elongated plug member 306 The apex of the plug member 306 is designated by the reference number 308.

The portion of the plug member 306 contiguous with the apex 308 defines the distally located portion 310 of the plug member, with the apex 308 forming the free end of the distally located portion. The remaining portion of the member 306 comprises the proximally located portion 312.

The retraction 304 means comprises a filament similar to that described above. The distal end of the filament 304 is connected to the apex of the plug member 306. The remainder of the filament 304 extends between the two legs 306A and 306B of the plug member 306 beyond the top (proximal) end thereof.

Like the other closure device embodiments described above, the distally located portion 310 of the plug member 306 is deformable, e.g., bendable. It particular, it can be bent to form a generally enlarged, somewhat mushroom shaped, head upon the retraction or pulling of the filament 304. That action occurs once the closure device 300 is in place within the puncture or incision 28 to be sealed.

Thus, the closure device 300, like the devices 100 and 300, is introduced by any suitable introducer through the puncture or incision so that its distal portion 310 is located within the interior of the artery and its proximal portion 312 is located within the puncture track 28A extending between the outer surface of the artery wall and the patient's skin as shown in FIG. 19.

In this position the extending portion of the filament 304 passes through incision or puncture track 28 to a point outside the body of the being.

The introducer is removed and the externally located extending portion of the filament 304 is then pulled away from the body, i.e., pulled in the proximal direction. This action causes the distally located portion of the plug member contiguous with the free end to begin to bend into a loop configuration as shown in FIG. 20. Continued pulling on the filament causes the free end of the tubular member 30 to flatten out into a generally mushroom shaped head which engages the inner surface of the artery wall contiguous with the incision or puncture therein as show in FIG. 21. This enlarged head has the effect of preventing the plug from exiting the artery through the puncture or incision and also effectively seals the puncture or incision so that blood cannot flow out of the artery through the puncture or incision.

Like the other embodiments of the closure devices described heretofore the enlarged head of the closure device 300 does not takes up a substantial portion of the interior of the artery and thus does not block off or otherwise impede the flow of blood therethrough. Moreover, like the closure devices 100 and 200 at least the distally located portion 310 of the plug means 302 is formed of a non-hemostatic material. In the embodiment shown herein, the entire member 302 is non-hemostatic, e.g., is formed of a sheet of polyglycolic acid, polylactide, polylactic acid, non-thrombogenic collagen. Thus, the head of the plug member which is located within the interior of the artery will not produce any blood clot(s) therein.

As should be appreciated from the foregoing the closure devices of the subject invention are very simple in construction and can be readily used to effectively and efficiently seal punctures or incisions in body organs or tissue, be they blood vessels, other lumens, ducts, etc. For example, the closure devices and their methods of use can be used for the purpose of sealing percutaneous transhepatic punctures to preclude the risk of bile leakage into the peritoneum, via the liver puncture site. Moreover, the devices and methods of use can be used for sealing percutaneous incisions in the lung or heart, such as could result from a wound.

Without further elaboration the foregoing will so fully illustrate our invention that others may, by applying current or future knowledge, adopt the same for use under various conditions of service.

What is claimed is:

1. A closure device for sealing a small incision or puncture i tissue separating a first internal portion of the body of a living being from a second internal portion thereof to prevent the flow of bodily fluid therebetween, said incision or puncture comprising a track portion extending through said first internal portion, said closure device comprising plug means and retraction means, said plug means comprising a generally elongated member having a central longitudinal axis, a distally located portion and a proximally located portion, said distally located portion of said elongated member being deformable and including a free end, said retracting means comprising a filament secured to said distally located portion of said plug means adjacent the free end thereof, said filament being connected to said distal portion of said elongated member adjacent the free end thereof and said filament having a first portion extending laterally of said central longitudinal axis of said elongated member along a first part of said distal portion of said elongated member for a portion of the length of said elongated member and said filament also having a second portion extending along a second part of said elongated member and closer to said central longitudinal axis of said elongated member than said first portion of said filament, said second portion of said filament extending out said proximal portion of said elongated member, said closure device being arranged to be positioned so that said distally located portion of said elongated member is disposed within said first internal portion of said body of said living being while said proximal portion of said elongated member is disposed within said track, and with said filament extending through said incision or puncture, said filament being arranged to be pulled to deform said distal portion of said plug means so that it cannot pass back through said incision or puncture and so that said incision or puncture is sealed by said deformed distal portion of said plug means.

2. The closure device of claim 1 wherein said distal portion of said plug means is non-hemostatic.

3. The closure device of claim 2 wherein said plug means comprises a tube, said tube having a central passageway, a proximal portion and a distal portion comprising an outside portion and a free end, said filament being connected to said distal portion of said tube adjacent the free end thereof and extending along the outside of said distal portion of said tube for a portion of the length of said tube and then passing into the central passageway of said tube and out said proximal portion thereof.

4. The closure device of claim 3 wherein said tube is formed of a rolled up sheet.

5. The closure device of claim 4 wherein said proximal portion of said plug means comprises a hemostatic material arranged to engage said body tissue contiguous with said track so that hemostasis occurs thereat to lock said closure device in place.

6. The closure device of claim 5 wherein said hemostatic material is expandable.

7. The closure device of claim 6 wherein said expandable material comprises crushed collagen.

8. The closure device of claim 5 wherein said sheet comprises a first portion of generally U-shape viewed plan and a second portion disposed within an interior space generally defined by the interior of said generally U-shaped first portion, said generally U-shaped first portion comprising said non-hemostatic material and said second portion comprising said hemostatic material, wherein when said sheet is rolled up to form said tube, said hemostatic material is generally located between said distal and proximal portions of said tube.

9. The closure device of claim 8 wherein said hemostatic material is expandable.

10. The closure device of claim 9 wherein said non-hemostatic material comprises polyglycolic acid and wherein said expandable hemostatic material comprises crushed collagen.

11. The closure device of claim 3 wherein said proximal portion of said plug means comprises a hemostatic material arranged to engage said body tissue contiguous with said track so that hemostasis occurs thereat to lock said closure device in place.

12. The closure device of claim 11 wherein said hemostatic material is expandable.

13. The closure device of claim 12 wherein said expandable material comprises crushed collagen.

14. The closure device of claim 2 wherein said distal portion of said plug means is comprised of a material selected from the group consisting of polyglycolic acid, polylactide, polylactic acid, and non-thrombogenic collagen.

15. The closure device of claim 14 wherein said proximal portion of said plug means comprises a hemostatic material arranged to engage said body tissue contiguous with said track so that hemostasis occurs thereat to lock said closure device in place.

16. The closure device of claim 15 wherein said hemostatic material is expandable.

17. The closure device of claim 16 wherein said expandable material comprises crushed collagen.

18. The closure device of claim 2 wherein said proximal portion of said plug means comprises a hemostatic material arranged to engage said body tissue contiguous with said track so that hemostasis occurs thereat to lock said closure device in place.

19. The closure device of claim 18 wherein said hemostatic material is expandable.

20. The closure device of claim 19 wherein said expandable material comprises crushed collagen.

21. The closure device of claim 1 wherein said plug means comprises a tube, said tube having a central passageway, a proximal portion and a distal portion comprising an outside portion and a free end, said filament being connected to said distal portion of said tube adjacent the free end thereof and extending along the outside of said distal portion of said tube for a portion of the length of said tube and then passing into the central passageway of said tube and out said proximal portion thereof.

22. The closure device of claim 21 wherein said tube is formed of a rolled up sheet.

23. A closure device for sealing a small incision or puncture in tissue separating a fist internal portion of the body of a living being from a second internal portion thereof to prevent the flow of bodily fluid therebetween, said incision or puncture comprising a track portion extending through said first internal portion, said closure device comprising plug means and retraction means, said plug means comprising a generally elongated member having a distally located portion and a proximally located portion, said distally located portion being deformable and including a free end, said plug means is formed of a sheet, said sheet being pleated to form a strip, said strip being bent in two at an apex thereof to form said generally elongated member, said retracting means comprising a filament secured to said apex of said distally located portion of said plug means forming the free end thereof, said closure device being arranged to be positioned so that said distally located portion is disposed within said first internal portion while said proximal portion thereof is disposed within said track, and with said filament extending through said incision or puncture, said filament being arranged to be pulled to deform said distal portion of said plug means so that it cannot pass back through said incision or puncture and so that said incision or puncture is sealed by said deformed distal portion of said plug means.

24. The closure device of claim 23 wherein said distal portion of said plug means is non-hemostatic.

25. The closure device of claim 24 wherein said distal portion of said plug means is selected of a material from the group consisting of polyglycolic acid, polylactide, polylactic acid and non-thrombogenic collagen.

26. A method of sealing of small incision or puncture in tissue separating a first internal portion of the body of a living being from a second internal portion thereof to prevent the flow of bodily fluid therebetween by use of a closure device, said incision or puncture comprising a track portion extending through said first internal portion, said closure device comprising plug means and retraction means, said plug means comprising a generally elongated member having a central longitudinal axis, a distally located portion and a proximally located portion, said distally located portion of said elongated member being deformable and including a free ned, said retracting means comprising a filament secured to said distally located portion of said plug means adjacent the free end thereof, said filament being connected to said distal portion of said elongated member adjacent the free end thereof and said filament having a first portion extending laterally of said central longitudinal axis of said elongated member along a first part of said distal portion of said elongated member for a portion of the length of said elongated member and said filament also having a second portion extending along a second part of said elongated member and closer to said central longitudinal axis of said elongated member than said first portion of said filament, said second portion of said filament extending out said proximal portion of said elongated member, said method comprising positioning said closure device so that said distally located portion of said elongated member, said method comprising positioning said closure device so that said distally located portion of said elongated member is disposed within said first internal portion of said body of said living being while said proximal portion of said elongated member is disposed within said track, and with said filament extending through said incision or puncture, and thereafter pulling on said filament to deform said distal portion of said plug means so that it cannot pass back through said incision or puncture and so that said incision or puncture is sealed by said deformed distal portion of said plug means.

27. The method of claim 26 wherein said distal portion of said plug means is non-hemostatic.

28. The method of claim 26 wherein said plug means comprises a tube, said tube having a central passageway, a proximal portion and a distal portion comprising an outside portion and a free end, said filament being connected to said distal portion of said tube adjacent the free end thereof and extending along the outside of said distal portion of said tube for a portion of the length of said tube and then passing into the central passageway of said tube and out said proximal portion thereof, whereupon when said filament is pulled it causes said distal end portion of said tube to bend over itself.

29. The method of claim 28 wherein at least said distal portion of said tube is formed of a non-hemostatic material so that it does not produce any blood clot within said blood vessel.

30. The method of claim 29 wherein said proximal portion of said plug means comprises a hemostatic material, and wherein said plug means is positioned so that said hemostatic material engages said body tissue contiguous with said track so that hemostasis occurs thereat to lock said closure device in place.

31. The method of claim 28 wherein said proximal portion of said plug means comprises a hemostatic material, and wherein said plug means is positioned so that said hemostatic material engages said body tissue contiguous with said track so that hemostasis occurs thereat to lock said closure device in place.

32. A closure device for sealing a small incision or puncture in tissue separating a first internal portion of the body of a living being from a second internal portion thereof to prevent the flow of bodily fluid therebetween, said incision or puncture comprising a track portion extending through said first internal portion, said closure device comprising plug means and retraction means, said plug means comprising a generally elongated member having a distally located portion and a proximally located portion, said distally located portion being deformable and including a free ned, said retracting means comprising a filament secured to said distally located portion of said plug means adjacent the free end thereof, said closure device being arranged to be positioned so that said distally located portion is disposed within said first internal portion while said proximal portion thereof is disposed and held within said track, and with said filament extending through said incision or puncture, said filament being arranged to be pulled to deform said distal portion of said plug means by bending the distal portion thereof in a direction generally towards said proximally located portion of said plug means, so that said distal end cannot pass back through said incision or puncture and so that said incision or puncture is sealed by said deformed distal portion of said plug means.

* * * * *